United States Patent [19]

Ionescu

[11] 4,240,443
[45] Dec. 23, 1980

[54] SELECTIVE PREAMPLIFIER OF CELL POTENTIALS

[75] Inventor: Vicentiu L. Ionescu, Bucharest, Romania

[73] Assignee: Institutul de Stiinte Biologice—Bucharest, Bucharest, Romania

[21] Appl. No.: 906,232

[22] Filed: May 10, 1978

[51] Int. Cl.³ ............................................. A61B 5/04
[52] U.S. Cl. .................................. 128/734; 128/902
[58] Field of Search ............ 128/2.1 R, 2.1 E, 2.1 M, 128/2.1 P, 2.06 B, 642, 734, 902

[56] References Cited
U.S. PATENT DOCUMENTS

| | | | |
|---|---|---|---|
| 3,498,288 | 3/1970 | Max et al. | 128/2.1 R |
| 3,580,243 | 5/1971 | Johnson | 128/2.06 B |

OTHER PUBLICATIONS

Allen et al., "An Automatic DC Level Comp. Circ. . . .", IEEE Trans. Bio. Med. Eng., vol. 20, Jan. 1973, pp. 58-60.
Belgum, "Automatic Offset of DC Membrane Potentials", Electroencephalography and Clin. Neur., vol. 42, No. 2, pp. 275-276, Feb. 1977.
Thompson et al., "An Improved Method for Extracellular Recording . . .", MBE, v. 13, #1, Jan. 1975, pp. 104-106.

Primary Examiner—Lee S. Cohen

[57] ABSTRACT

There is disclosed an apparatus for the selective detection and controlled gain of intranuclear and intracellular potentials. Such apparatus contains an amplifier with a gain control, such amplifier having an input terminal and an output terminal and several stages each containing an integrated active electronic device. The input terminal is the input terminal of the integrated active device of the first stage, such input terminal being directly coupled by a double screened lead with a metallic microelectrode for collecting intracell and intranuclear biopotentials. The apparatus further includes a circuit for isolating the reference point of the first said stage, as compared to the null point of the power supply of the said apparatus, so that the reference point of the first stage floats according to the bioelectric signal applied at the input of the first stage, and a circuit for neutralizing the offset voltages in the stages of said amplifier, thus obtaining a good equality between the floating potential of the reference point of the first stage and the potential applied at the input terminal of the same stage. In a preferred embodiment the amplifier is directly coupled with the input terminal of a variable time constant integrator, and the stages of the amplifier are directly coupled without the use of any capacitors, thereby obtaining an improved signal to noise ratio.

6 Claims, 1 Drawing Figure

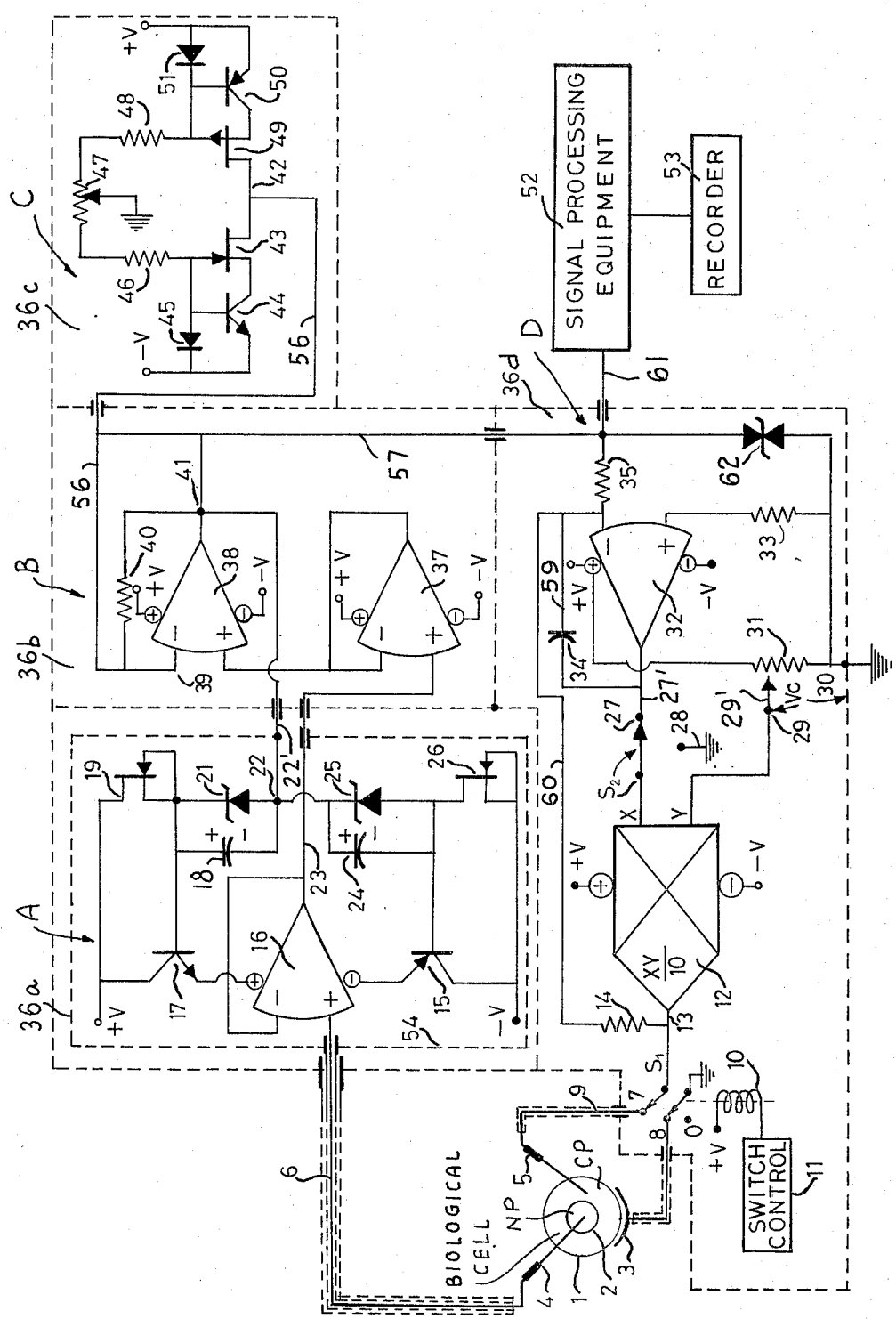

SELECTIVE PREAMPLIFIER OF CELL POTENTIALS

BACKGROUND OF THE INVENTION

1. Field of the Invention

This invention lies in the field of electronic sensors of bioelectrical potentials, and more particularly relates to an improved electronic device for collecting and selecting the biopotentials existing between the cell and the medium outside the nucleus membrane as a consequence of the metabolical activity of the cell under study.

1. Description of the Prior Art

Systems for detecting cell biopotentials are conventionally characterized by a microelectrode introduced into the nucleoplasma or cytoplasma and another electrode which is placed at random in the close neighborhood outside the nuclear or cell membrane. The bioelectrical resting or action potentials supplied by the metabolical activity of the cell are led by means of microelectrodes and connections to an electronic device for adaptation and amplification, as well as to processing and record circuits.

The requirements for intracell measurements are very severe; some sensitive neurons may tolerate without destroying a straight flow current of some tenths of picoamperes, so that the input flow of current to the preamplifier may, in the worst case, be a maximum of 0.5 picoamperes. The value of the resting potential of the cell membrane is a maximum of 100 milliVolts (mV) in most cases (Bures, J. et al. Electrophysiological methods in biological research, Prague 1967), and the resting potentials of the nuclear membrane is about $-12$ mV(Loewenstein, W. R. and Kanno, Y., Nature, 1962, 195:462–464); the finite input impedance of the measurement amplifier, which is the load of the cell, must be at least 100 GigaOhms for causing a flowing stream under 0.12 pAmps. The action potentials are often measured; they include some rapid signals like a sharp impulse whose rise time is of 50–100 microseconds and having a duration of 0.2–15 milliseconds. For transmitting such impulses a considerable decrease of the capacity of the cable to the preamplifier and its input capacity is necessary.

When a metal microelectrode is introduced into the cell, the potential appearing between the microelectrode terminal and reference microelectrode is the sum of three potentials, (1) the contact metal-electrolyte potential, (2) the membrane cell potential, and (3) the contact potential between the reference electrode and the extracell surroundings.

When the membrane potential is measured, the sum of the other two terms is assured to be constant (Electrodes and the measurement of bioelectric events, by Geddes, L. A., Wiley-Interscience, 1972).

When the microelectrode is introduced into the cell nucleus, the output potential is made up of four potentials: (1) the contact metal-nuclear electrolyte potential, (2) the nucleus membrane potential, (3) the cell membrane potential, and (4) the contact potential between the reference electrode and the extracell space. See "Some electrical properties of a nuclear membrane examined with a microelectrode," W. R. Loewenstein and Kanno, "The Journal of General Physiology, Vol. 46, 1963."

The potential generated at the level of nuclear membrane has a smaller amplitude and time constant than in the cell membrane. As a result, the action potential due to nucleus depolarization has a shorter duration that the one released at the cell membrane level, (Lowenenstein and Kanno, 1962-1963).

In pursuit of the objective of a biopotential preamplifier having a high impedance with an effective reduction of its input capacity and having the possibility of automatic compensation of direct current levels which drain in the amplification chain, including the rest potential of the cell, an electronic device has been achieved containing a commercial cathode follower with input capacity neutralizing and a circuit for the automatic compensation of the direct current level. See: "An Automatic D.C.-Level Compensation Circuit for Electrophysiology," G. I. Allen and K. Toyama, "IEEE Transactions of Biomedical Engineering, Vol. 20, Jan. 1973."

Although commercial preamplifiers with unitary gain of the cathode follower type, as (MPA-5 Transidyne General, Ann Arbor, Michigan; Fantron Amplifier Mod. 5791, Basel, Switzerland; Microelectrode Preamplifier Type 3111; Narco Bio-Systems Inc., Houston, Tex., etc.) offer a high input impedance and a substantial reduction of input capacity, by manual neutralization, nevertheless the noise at the amplifier non inverse input due to positive capacity feedback remains in the range of 30-70 micro Volts rms.

By using an automatic compensation device for D.C. level (Allen and Toyama, 1973) in measuring the nuclear potentials, some valuable informations can remain unobserved due to integration with a fixed constant time, as well as its inversion circuit.

A considerable increase of the signal-noise ratio and accuracy of unitary amplification of biopotentials, both nuclear and cellular, may be obtained by a more accentuated reduction of the noise produced at the preamplifier input, as well as by creating a controlled selection of certain action potentials according to the electrical parameters of the two membranes: nuclear and cellular, implied in their production.

SUMMARY OF THE INVENTION

A principal object of the invention is to provide an apparatus for the selective detection and amplification of intracell potentials assuring a maximum output signal to a noise ratio.

Another object of the invention is to provide a preamplifier with unitary gain control combined with an optional neutralization circuit of components supplying continuous current levels and the selection according to duration, controlled in voltage, of the action potentials emitted between the nucleus and the exterior of the biological cell.

Consequently this invention provides an apparatus with a preamplifier for the selective detection of intracell biopotentials, such apparatus containing a very high input impedance unitary gain preamplifier having the input terminal coupled by means of a short double-screened cable with the biopotential collection microelectrode and an inversion and integration circuit with an adjustable time constant, such circuit being controlled in voltage the output terminal of such circuit being connected to the reference electrode placed in the neighborhood of the cell to be studied. In the illustrative embodiment the amplifier is made up of three directly coupled stages, the first stage containing an FET input operational amplifier having a floating reference point, the output of the first stage being coupled with the input terminal of a pair of two operational amplifiers with unitary gain control connected in cascade. The output of this three-stage amplifier is coupled directly with the floating reference point of the first stage for increasing its reference potential to the value of the biological signal applied to the input terminal. As a consequence the amplifier has an increased resistance and a decreased input capacity.

The input of the inversion and integration circuit is connected to the output of the three-stage amplifier group. The voltage-controlled integration circuit is made up of an operational amplifier working as integrator-inverting circuit and an electronic multiplier placed in the second loop at the inverting input of the operational amplifier.

Since the reaction is multiplied by a control voltage, the integration time constant can be adjusted or modified between certain limits.

This integration and inversion circuit, connected as above, applies in antiphase by means of the biological cell a potential that neutralizes any potentials of direct current in the collection and amplification chain as well as certain action potentials having a higher duration than the time constant of the integrator.

BRIEF DESCRIPTION OF THE DRAWING

The single FIGURE of the drawing is an electric diagram with three electrodes, a biological cell, an amplifier with unitary gain, and two neutralization circuits.

DESCRIPTION OF THE PREFERRED EMBODIMENT

Referring to the drawing, there is schematically shown a biological cell that contains a cell membrane 1, a nuclear membrane 2, a cytoplasma CP held between membrane 1 and 2, and a nucleoplasma NP held inside membrane 2. A microelectrode 4 is introduced into the nucleoplasma and a reference microelectrode 5 is introduced into the cytoplasma. Both microelectrodes 4 and 5 are metallic, are covered with glass, and have a maximum diameter of 0.5 microns. An electrode 3 disposed outside membrane 1 is connected by a shielded lead to a terminal 8 of a switch $S_1$ of the apparatus of the invention. Electrode 5 is connected to a terminal 7 of the switch $S_1$ by a shielded lead 9. Electrode 4 is connected by a double shielded lead 6 to the input of the first stage 16 of the amplifier of the apparatus.

The stage 16 of the amplifier and its attendant components are housed within a first, inner shield 54. The remainder of the apparatus, with the exception of a signal processing equipment 52 and a recorder 53 are housed within connected compartments 36a–36d of a second shield. As shown, shield 54 is not grounded, whereas shields 36a–36d are grounded. The apparatus contained within the inner shield 54 and the outer shield section 36a, which is composed of the first amplifier stage 16 and its attendant components, is generally designated by the reference character A. The apparatus contained in shield section 36b, which is designated B, is composed of a matched pair of voltage follower amplifiers, connected in cascade, and in series with the amplifier stage 16. The apparatus contained within shield section 36c, designated C, is an inversion cancelling circuit of offset voltage. The apparatus contained within shield section 36d, designated D, includes an amplifier stage 32 and its attendant components constituting an integrator with an adjustable time constant, and a multiplier 12.

The reference electrode 3, disposed in the extracellular space outside and in the neighborhood of the cell membrane 1, is selectively connected to the output terminal 13 of the electronic multiplier 12 or to ground by means of the two-pole switch $S_1$ the movable contactors of which are selectively shifted between their upper and lower positions by means of a solenoid 10 and a switch control 11 for selectively energizing and de-energizing the solenoid. When the contactors of switch $S_1$ are in their upper position, as shown in the drawing, and the microelectrode 4 is introduced into the nucleoplasma NP, the biopotentials generated at the level of nuclear membrane 2 are exclusively measured. When the contactors of switch $S_1$ are in the lower position, the upper contactor connects the reference electrode 3 by way of the shielded lead therefrom to the terminal 8 of the switch $S_1$ and thence to the terminal 13 of the electronic multiplier 12, so that the biopotentials can be simultaneously measured at the level of the cell membrane 1 and the nuclear membrane 2.

By advancing the microelectrode 5 introduced into the cytoplasma CP under microscopy control, and with the contactors of the switch $S_1$ in their lower position, the biopotentials supplied at the level of the cell membrane 1 can be measured.

UNIT A OF THE APPARATUS

The double-shielded lead 6 from the electrode 4 is connected to the first or plus voltage follower input of the first amplifier stage 16, the inner shield of lead 6 being connected to the shield 54, and the outer shield of lead 6 being connected to the outer shield section 36a. Amplifier 16 may be one sold under the designation "Analog devices FET-input, AD515 L." Such amplifier 16 has a bias current as low as 75 Femto amps. and an offset voltage below 1.0 mVolts.

The output of amplifier 16 is connected by a wire 23 which extends through the shields 54 and 36a to the input (+ terminal) of a second stage 37 of the amplifier located within section B of the apparatus. Stage 37 will be described in detail hereinafter. A wire connects the wire 23 leading from amplifier 16 to the minus input terminal of such amplifier. The minus terminal $-V$ of the power source is connected to the minus power input terminal of the amplifier 16 through a p-n-p transistor 15, the collector of such transistor being connected to the terminal $-V$, the emitter of transistor 15 being connected to the minus power terminal of the amplifier 16. The collector of the transistor 15 is also connected to the gate and to the source of a n-channel FET (field effect transistor) 26, the base of transistor 15 being connected to the drain of the FET 26.

The drain of FET 26 is connected through series connected, similarly disposed zener diodes 25 and 21 to the source and gate of a second n-channel FET 19. A condensor 24 is shunted across zener diode 25, and a condensor 18 is shunted across zener diode 21. The cathode of zener diode 21 is connected to the source and gate of FET 19 and to the base of an n-p-n transistor 17, the emitter of which is connected to the plus power supply terminal of the amplifier 16. The plus terminal of the power supply, $+V$ is connected to both the collector of transistor 17 and to the drain of the n-channel FET 19.

Because of the floating voltage source provided by the bipolar and monopolar transistors 15, 17 and 19, 26, respectively, as well as the reaction by means of the zener diodes 21 and 25 in parallel with the condensers 18 and 24, the reference point 22, disposed between the zener diodes 21 and 25, is isolated from the power supply ($\pm V$ null point), a constant voltage being supplied equal to and of contrary sign to the power of feeding terminals, plus and minus, of the amplifier 16.

PORTION B OF THE APPARATUS

The output of amplifier stage 16 is connected directly through wire 23 to the plus input terminal of a second stage 37 of the amplifier group, the output of stage 37 being directly connected to the plus input terminal of a third amplifier stage 38. The output from stage 37 is also connected to the minus input terminal of stage 37, the output of stage 38 being connected through a resistor 40 to the minus input terminal of stage 38. The reference point 22 in unit A is connected through a wire 22' to the output terminal 41 of the amplifier stage 38.

The amplifier stages 37 and 38 constitute a matched pair of cascade connected voltage followers which may be, for example, those sold under the trade designation "Burr-Brown 3500 MP matched pair MPIC."

The amplifier stages 37 and 38 apply to the reference point 22 a voltage which equals the value of the potential applied to the input of the amplifier stage 16, thus reducing the input capacity in the amplifier stage 16 by an approximate factor of $(1/A_1 + 1/A_2 + 1/A_3)$, and increasing the input resistance of amplifier stage 16 by a reciprocal of the same factor by which the capacity of stage 16 was reduced. $A_1$, $A_2$, $A_3$ are the open loop gains of the amplifier stages 16, 37, 38, respectively. By the above-described means, and by the connection of the screen 54 as well as the inner screen of the cable 6 to the floating reference point 22, and the outer screen of cable 6 to ground, as shown at the bottom of section 36d of the screen, there is obtained in the non-inverting input of amplifier stage 16 an input resistance higher than $10^{13}$ Ohms and an input capacity below 0.01 pico Farads. Opposed zener diodes 62, disposed in unit D, to be described, prevents the latch-up of the amplifier 16, 37 and 38 during the functioning commands of the sources of constant current, together with the coupling of the stabilized power supply $\pm V$, which is disposed in unit C of the apparatus.

UNIT C OF THE APPARATUS

Connected to the minus input terminal 39 of the amplifier stage 38 is a wire 56 leading from the output terminal of unit C. Unit C is a circuit for providing an offset voltage to cancel the voltage which appears on the amplifier chain 16, 37 and 38. Such circuit applies to the minus terminal 39 of amplifier stage 38 a current that determines in the reaction resistance 40 a voltage contrary to the offset voltages that may appear at the output terminal 41 of the amplifier stage 38.

The unit C includes a power supply terminal $+V$ which is connected to the emitter of a p-n-p transistor 50 the collector of which is connected to the source of a p-channel FET 49, the gate of which is connected through a resistor 48 to a first end of the winding of a nulling potentiometer 47. The anode of a diode 51 is connected to the voltage source $+V$, the cathode of diode 51 being connected to the gate of transistor 49 and the base of transistor 50; the collector of transistor 50 is connected to the source of a p-channel FET 49.

The negative terminal $-V$ of the power source is connected to the emitter of an n-p-n transistor 44, the collector of which is connected to the source of an n-channel FET 43. The emitter of transistor 43 is connected through a resistor 46 to the second end of the winding of potentiometer 47, the adjustable slider of which is connected to ground, as shown. Terminal $-V$ is also connected, to the base of transistor 44 through a diode 45, the anode of diode 45 being connected to the gate of transistor 43, the cathode of diode 45 being connected to the negative power terminal $-V$. The base of transistor 44 is connected to the gate of transistor 43. The drains of transistors 43 and 49 are connected to a common wire 42 which is connected to the wire 56 leading to the negative input terminal 39 of the third amplifier stage 38.

By means of nulling potentiometer 47, the differences between the outputs of the two sources of constant current in the unit C, converging to the point 42, are closed in order to supply the current difference that flows through resistance 40 to neutralize the offset voltage described above. The neutralization circuit of the offset voltage assures a perfect equality between the potential applied to the input terminal of amplifier stage 16 and the potential from the floating null point 22, thus to obtain a maximum input impedance at the input of the amplifier stage 16.

UNIT D OF THE APPARATUS

Unit D includes an amplifier 32 which may be one sold under the trade designation "Burr—Brown 3527 FET-input Low Drift," and an integrated electronic multiplier 12, which may be one sold under the trade designation "Analog devices AD 435-J." Amplifier 32 and multiplier 12 together form an integrator with an adjustable time constant. A wire 57 connected to wire 56 is connected to ground through the above-described opposed zener diodes 62 the cathodes of which are connected. A resistor 35 is connected between wire 57 and the negative input terminal of the amplifier 32. A condenser 34 interposed in a wire 59 extending between the negative input terminal of amplifier 32 and its output terminal 27 and the resistance 35 are the elements of the integrator with a fixed (but adjustable) time constant formed by means of the amplifier 32. A resistance 33 is connected between ground and the positive input terminal of the amplifier 32.

The negative input terminal of amplifier 32 is connected by a wire 60, in which a resistance 14 is interposed, to the output terminal 13 of the multiplier 12. A first input X of the multiplier 12 is selectively connected by a switch $S_2$ to a terminal 27 connected to the output wire 27' of the amplifier 32 when the movable contactor of switch $S_2$ is in its upper position, as shown in the drawing. When such contactor is in its lower position, the input terminal X of the multiplier 12 is connected to terminal 28 which in turn is connected to ground.

A second input terminal Y of multiplier 12 is connected through a terminal 29 to the movable slider 29' of a potentiometer 31. The winding of potentiometer 31 is connected between ground and the positive power supply terminal of the amplifier 32.

Resistance 33 is established at a value that allows the maximum reduction of the polarization current in the amplifier 32. Multiplier 12 together with the resistance 14 forms the second reaction loop for the integrator with the amplifier 32. Because this reaction is multiplied by control voltage $V_c$, greater than or equal to 0, that is collected at the slider 29' of the potentiometer 31, the integrator time constant with the amplifier 32 is reduced. The result of this decrease is a time constant controlled by voltage $V_c$ existing between points 29 and 30.

The biological signals with a longer duration than the fixed time constant adjusted a priori by the value of $V_c$ are practically neutralized through the integration circuit and appears at the output terminal, but in antiphase with the biopotentials collected by the microelectrode 4. Because of this, there appear at the output terminal 41 of the preamplifier only those bioelectrical signals with a shorter duration than the time constant of the $V_c$ commanded integrator. The integration and neutralization circuit with the multiplier 12 and amplifier 32 can be inhibited by connecting the input X of the multiplier 12 to the ground terminal 28 by means of switch $S_2$ so that the reference electrodes 3 and 5 are connected to ground by the output impendance of multiplier 12.

The output from stage 38 of the preamplifier is led by way of terminal 41, wire 57, and a further wire 61 connected thereto to signal processing equipment 52 and thence to a recorder 53 or the like.

Although the invention is illustrated and described with reference to one preferred embodiment thereof, it is to be expressly understood that it is in no way limited to the disclosure of such a preferred embodiment, but is capable of numerous modifications within the scope of the appended claims.

What is claimed is:

1. Apparatus for the selective detection and amplification of intranuclear and/or intracellular biopotentials comprising:

a first metallic microelectrode for collecting the intracellular and/or intranuclear action biopotentials adapted to be inserted into a biological cell;

a double screened central wire lead having two screening sheaths connected to said first metallic microelectrode;

an amplifier with unity gain control having a sufficient sensitivity to action biopotentials released by cells with a very high internal resistance, the amplifier having an input terminal and an output terminal and a plurality of stages, the input terminal of said amplifier being the input terminal of the first stage of the amplifier, said input terminal being directly coupled with the said first metallic microelectrode through the central wire of the said double screened lead, the first stage of the amplifier having a floating reference point;

a power supply circuit providing the feeding terminals of all active and passive electronic circuits and components of the said apparatus with two equal and of contrary sign stabilized voltages in comparison with a grounded null point;

first circuit means electrically connected to and separating the said floating reference point of the first stage of the amplifier from the said power supply grounded null point;

second circuit means for neutralizing the offset voltages in the stages of the said amplifier, whereby to obtain a good equality between the potential of the said floating reference point of the first stage of the amplifier and the biopotential applied, by means of said metallic mircoelectrode and said double screened lead wire to the input terminal of the said first stage, and an extremely low input capacity as well as high input resistance to the input terminal of said first stage of the amplifier;

a second metallic microelectrode functioning as a first reference electrode means for the power supply circuit allowing the first microelectrode to collect the intranuclear biopotentials only and adapted to be inserted in said biological cell; and a third metallic electrode functioning as a second reference electrode means for the power supply circuit, adapted to be placed closely upon the outer surface of the cell, for allowing the first microelectrode to collect the intracellular biopotentials or both intranuclear and intracellular ones, in relation to the tip position of said first metallic microelectrode in the interior plasma of the cell under study.

2. Apparatus according to claim 1, wherein each of the stages of the said amplifier contains an integrated active electronic device, and the input terminal of the amplifier is the input terminal of the integrated active device of the first stage of the amplifier.

3. Apparatus according to claim 1, comprising:

a fist screen surrounding the first stage of the amplifier circuit;

means connecting said first screen to the inner screening sheath of the said double-screened lead wire, as well as the floating reference point of the said first stage of the amplifier;

a second screen surrounding and separated from the first screen and surrounding the remainder of the recited apparatus;

circuit means connecting the said second screen to the other screening sheath of the double-screened lead wire as well as to the grounded null point of the said power supply, whereby to obtain a reduced input capacity to the input of the said double-screened lead wire connected to the said first stage of the amplifier.

4. The apparatus according to claim 1, wherein the said amplifier contains three unit gain controlled stages, the amplifier stages being directly coupled, whereby to obtain an improved signal to noise ratio.

5. The apparatus according to claim 1, comprising an adjustable time constant integrator, and circuit means directly coupling the output terminal of said amplifier with the input terminal of the adjustable time constant integrator.

6. Apparatus for monitoring, selection according to duration, and the amplification of intranuclear and/or intracellular action biopotentials, comprising:

a first metallic microelectrode;

second and third electrode functioning as reference electrodes;

a unity gain controlled preamplifier having an input terminal and an output terminal, the input terminal being directly connected to the said first metallic microelectrode by means of a double-screened lead wire;

a selectively operated circuit for inversion and integration, said inversion and integration circuit having an adjustable time constant integrator and an output terminal, coupled in such a way as to release from its output terminal only those biopotentials having their width duration greater than a pre-established time constant of said integrator;

means including a first switch and a second switch, said first switch connecting the said output terminal of the said integrator to the second reference electrode of the apparatus, or with an automatic command furnished at a given time by a programmed switch control circuit to the said third reference electrode, in such a way as to obtain only selected intranuclear biopotentials, respectively intracellular, or, if any, selected intranuclear biopotentials from the intracellular ones for a time constant of the integrator greater than the duration of the nuclear biopotentials and less than the cellular ones as given by:

said second switch adapted to be manually activated and inhibiting on a lower activated position the selection process of the cell biopotentials.

* * * * *